(12) United States Patent
Folan et al.

(10) Patent No.: US 11,944,557 B2
(45) Date of Patent: Apr. 2, 2024

(54) SELF EXPANDING STENT WITH COVERING

(71) Applicant: BOSTON SCIENTIFIC SCIMED, INC., Maple Grove, MN (US)

(72) Inventors: Martyn G. Folan, Galway (IE); Daniel Tuck, Galway (IE); Gary Gilmartin, Foxford (IE); Michael Rodgers, Mayo (IE)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 143 days.

(21) Appl. No.: 17/460,654

(22) Filed: Aug. 30, 2021

(65) Prior Publication Data
US 2022/0062016 A1 Mar. 3, 2022

Related U.S. Application Data

(60) Provisional application No. 63/072,621, filed on Aug. 31, 2020.

(51) Int. Cl.
*A61F 2/852* (2013.01)
*A61F 2/89* (2013.01)
*A61F 2/04* (2013.01)
*A61F 5/00* (2006.01)

(52) U.S. Cl.
CPC .............. *A61F 2/852* (2013.01); *A61F 2/89* (2013.01); *A61F 2002/045* (2013.01); *A61F 5/0083* (2013.01); *A61F 2210/0076* (2013.01)

(58) Field of Classification Search
CPC .... A61F 2/852; A61F 2/89; A61F 2210/0076; A61F 2250/0007; A61F 2250/0009
See application file for complete search history.

(56) References Cited

U.S. PATENT DOCUMENTS

| | | |
|---|---|---|
| 4,553,545 A | 11/1985 | Maass et al. |
| 4,776,337 A | 10/1988 | Palmaz |
| 5,064,435 A | 11/1991 | Porter |

(Continued)

FOREIGN PATENT DOCUMENTS

| | | | |
|---|---|---|---|
| JP | 2000279532 A | 10/2000 | |
| WO | 9600103 A1 | 1/1996 | |

(Continued)

OTHER PUBLICATIONS

International Search Report and Written Opinion dated Dec. 3, 2021 for International Application No. PCT/US2021/048178.

(Continued)

*Primary Examiner* — Paul B Prebilic
(74) *Attorney, Agent, or Firm* — Seager, Tufte & Wickhem, LLP

(57) ABSTRACT

An endoprosthesis may include an expandable framework configured to shift between a delivery configuration and a deployed configuration, and a covering including a plurality of polymeric cover segments disposed about at least a portion of the expandable framework. A portion of each of the plurality of polymeric cover segments may be fixedly attached to the expandable framework. The plurality of polymeric cover segments is longitudinally spaced apart from each other in the delivery configuration. The plurality of polymeric cover segments longitudinally overlaps each other in the deployed configuration.

20 Claims, 12 Drawing Sheets

(56) References Cited

U.S. PATENT DOCUMENTS

| | | | |
|---|---|---|---|
| 5,425,765 A | 6/1995 | Tiefenbrun et al. | |
| 5,445,646 A | 8/1995 | Euteneuer et al. | |
| 5,676,696 A * | 10/1997 | Marcade | A61F 2/07 606/191 |
| 5,709,713 A * | 1/1998 | Evans | A61F 2/07 623/1.53 |
| 5,824,046 A | 10/1998 | Smith et al. | |
| 6,042,605 A | 3/2000 | Martin et al. | |
| 6,099,559 A | 8/2000 | Nolting | |
| 6,099,561 A | 8/2000 | Alt | |
| 6,120,536 A | 9/2000 | Ding et al. | |
| 6,139,573 A | 10/2000 | Sogard et al. | |
| 6,143,022 A | 11/2000 | Shull et al. | |
| 6,156,064 A | 12/2000 | Chouinard | |
| 6,159,239 A | 12/2000 | Greenhalgh | |
| 6,162,244 A | 12/2000 | Braun et al. | |
| 6,165,211 A | 12/2000 | Thompson | |
| 6,168,619 B1 | 1/2001 | Dinh et al. | |
| 6,254,627 B1 | 7/2001 | Freidberg | |
| 6,315,794 B1 | 11/2001 | Richter | |
| 6,319,278 B1 | 11/2001 | Quinn | |
| 6,334,867 B1 | 1/2002 | Anson | |
| 6,352,553 B1 | 3/2002 | Van Der Burg et al. | |
| 6,364,904 B1 | 4/2002 | Smith | |
| 6,645,242 B1 | 11/2003 | Quinn | |
| 6,790,225 B1 | 9/2004 | Shannon et al. | |
| 7,118,592 B1 | 10/2006 | Dang et al. | |
| 7,425,219 B2 | 9/2008 | Quadri | |
| 7,645,298 B2 | 1/2010 | Hartley et al. | |
| 7,828,837 B2 | 11/2010 | Khoury | |
| 8,147,538 B2 | 4/2012 | Brown et al. | |
| 8,167,926 B2 | 5/2012 | Hartley et al. | |
| 8,231,665 B2 | 7/2012 | Kim et al. | |
| 8,317,854 B1 | 11/2012 | Ryan et al. | |
| 9,056,001 B2 | 6/2015 | Armstrong et al. | |
| 10,154,917 B2 | 12/2018 | Bogert | |
| 10,405,966 B2 | 9/2019 | Johnson | |
| 2001/0021870 A1 | 9/2001 | Edwin et al. | |
| 2001/0032009 A1 | 10/2001 | Layne et al. | |
| 2001/0039446 A1 | 11/2001 | Edwin et al. | |
| 2002/0002397 A1 | 1/2002 | Martin et al. | |
| 2003/0199967 A1 | 10/2003 | Hartley et al. | |
| 2004/0054397 A1 | 3/2004 | Smith et al. | |
| 2004/0087886 A1 | 5/2004 | Gellman | |
| 2005/0059923 A1 | 3/2005 | Gamboa | |
| 2007/0032857 A1 | 2/2007 | Schmid et al. | |
| 2007/0142904 A1 | 6/2007 | Sorenson et al. | |
| 2007/0219612 A1 | 9/2007 | Andreas et al. | |
| 2008/0140176 A1 | 6/2008 | Krause et al. | |
| 2010/0100170 A1 | 4/2010 | Tan et al. | |
| 2011/0022154 A1 | 1/2011 | Hamer et al. | |
| 2012/0130472 A1 | 5/2012 | Shaw | |
| 2012/0193018 A1 | 8/2012 | Banas et al. | |
| 2012/0239134 A1 | 9/2012 | Dierking | |
| 2012/0296406 A1 | 11/2012 | Minion | |
| 2013/0144373 A1 * | 6/2013 | Shahriari | A61F 2/2418 623/1.13 |
| 2013/0204343 A1 | 8/2013 | Shalev | |
| 2013/0261731 A1 | 10/2013 | Zhou et al. | |
| 2013/0274851 A1 | 10/2013 | Kelly | |
| 2015/0005869 A1 * | 1/2015 | Soletti | A61F 2/064 623/1.13 |
| 2015/0223925 A1 | 8/2015 | Rasmussen et al. | |
| 2016/0058585 A1 | 3/2016 | Seddon et al. | |
| 2019/0151072 A1 | 5/2019 | Walzman | |
| 2020/0163750 A1 * | 5/2020 | Ehnes | A61F 2/07 |
| 2022/0062016 A1 * | 3/2022 | Folan | A61F 2/04 |

FOREIGN PATENT DOCUMENTS

| | | | |
|---|---|---|---|
| WO | 1998008456 A1 | 3/1998 | |
| WO | 9915105 A1 | 4/1999 | |
| WO | 2001001886 A1 | 1/2001 | |
| WO | 2009145901 A1 | 12/2009 | |
| WO | 2011076408 A1 | 6/2011 | |
| WO | 2013123147 A1 | 8/2013 | |
| WO | 2014107748 A2 | 7/2014 | |
| WO | WO-2019014634 A1 * | 1/2019 | A61F 2/07 |

OTHER PUBLICATIONS

International Search Report from PCT/2014/020086 dated Jun. 24, 2014.

* cited by examiner

content continues …

SELF EXPANDING STENT WITH COVERING

CROSS REFERENCE TO RELATED APPLICATIONS

This application claims the benefit of and priority to U.S. Provisional Patent Application Ser. No. 63/072,621 filed on Aug. 31, 2020, the disclosure of which is incorporated herein by reference.

TECHNICAL FIELD

The present disclosure pertains to medical devices, and methods for manufacturing and/or using medical devices. More particularly, the present disclosure pertains to an improved design for an endoprosthesis or stent.

BACKGROUND

Current braided or knitted self-expanding stents may express a large degree of longitudinal flexibility due to design and device length. This may be advantageous for the purpose of device delivery, especially in more tortuous anatomical regions and for reduction in lumen straightening post-delivery, which is typically seen as being less traumatic on target lumens. In some cases, a bare stent may include an additional coating where benign strictures are to be treated, stent removal may be a requirement, and/or where the coating is used to isolate a treated lumen from nutritional impaction (e.g., post bariatric surgery leak treatment, fistula treatment, etc.). Ideally, the flexibility of the base stent would be mimicked by the coated version of the stent for similar deliverability and anatomical modeling reasons. However, coated versions of a bare self-expanding stent do not typically express similar flexibility due to limitations of the coating. Efforts to counteract this may include thinning out the coating, which may positively impact flexibility but negatively impact coating fatigue and durability. The use of more advanced materials as an alternative may be cost prohibitive. Additionally, coated stents may be susceptible to reduced side branch access where placement of the coated stent in a primary lumen needing treatment could block off an adjacent, intersecting lumen that may simultaneously need drainage. Some examples of this include the branches of the biliary tree from pancreatic duct blockage up to higher hilar region blockages. There is an ongoing need to provide alternative endoprostheses or stents as well as alternative methods for manufacturing and using endoprostheses or stents which may include a coating that negligibly impacts underlying stent flexibility while providing economical manufacturing costs, effective leak resistance, stent removability, and/or side branch access characteristics.

SUMMARY

In a first aspect, an endoprosthesis may comprise an expandable framework configured to shift between a delivery configuration and a deployed configuration, and a covering comprising a plurality of polymeric cover segments disposed about at least a portion of the expandable framework. A portion of each of the plurality of polymeric cover segments may be fixedly attached to the expandable framework. The plurality of polymeric cover segments may be longitudinally spaced apart from each other in the delivery configuration. The plurality of polymeric cover segments may longitudinally overlap each other in the deployed configuration.

In addition or alternatively to any aspect discussed herein, each of the plurality of polymeric cover segments extends circumferentially about an entire circumference of the expandable framework.

In addition or alternatively to any aspect discussed herein, the covering extends between a first end of the expandable framework and a second end of the expandable framework.

In addition or alternatively to any aspect discussed herein, each of the plurality of polymeric cover segments includes an attachment band and a free end opposite the attachment band.

In addition or alternatively to any aspect discussed herein, the attachment band of each of the plurality of polymeric cover segments is oriented towards a first end of the expandable framework.

In addition or alternatively to any aspect discussed herein, the free end of each of the plurality of polymeric cover segments is oriented towards a second end of the expandable framework.

In addition or alternatively to any aspect discussed herein, the attachment band is discontinuously attached to the expandable framework.

In addition or alternatively to any aspect discussed herein, and in a second aspect, an endoprosthesis may comprise an expandable framework configured to shift between a delivery configuration and a deployed configuration, and a covering comprising a plurality of polymeric cover segments disposed about the expandable framework and extending longitudinally along the expandable framework. The covering may extend discontinuously between a first end of the expandable framework and a second end of the expandable framework in the delivery configuration. The covering may extend continuously from the first end of the expandable framework to the second end of the expandable framework in the deployed configuration.

In addition or alternatively to any aspect discussed herein, the expandable framework includes a plurality of cells. In the delivery configuration, at least some cells of the plurality of cells are completely uncovered by the covering.

In addition or alternatively to any aspect discussed herein, in the deployed configuration, all cells of the plurality of cells are completely covered by the covering.

In addition or alternatively to any aspect discussed herein, the expandable framework is self-expanding.

In addition or alternatively to any aspect discussed herein, each of the plurality of polymeric cover segments extends circumferentially about an entire circumference of the expandable framework.

In addition or alternatively to any aspect discussed herein, a free end of a first polymeric cover segment of an adjacent pair of polymeric cover segments is longitudinally spaced apart from of an attachment band of a second polymeric cover segment of the adjacent pair of polymeric cover segments in the delivery configuration.

In addition or alternatively to any aspect discussed herein, the free end of the first polymeric cover segment of the adjacent pair of polymeric cover segments is disposed radially outward of the attachment band of the second polymeric cover segment of the adjacent pair of polymeric cover segments in the deployed configuration.

In addition or alternatively to any aspect discussed herein, and in a third aspect, an endoprosthesis may comprise an expandable framework configured to shift between a delivery configuration and a deployed configuration, and a covering comprising a plurality of polymeric cover segments disposed about at least a portion of the expandable framework. An attachment portion of each of the plurality of polymeric cover segments may be fixedly attached to the expandable framework. The plurality of polymeric cover segments may longitudinally and circumferentially overlap each other.

In addition or alternatively to any aspect discussed herein, none of the plurality of polymeric cover segments is directly attached to another of the plurality of polymeric cover segments.

In addition or alternatively to any aspect discussed herein, the attachment portion of each of the plurality of polymeric cover segments is disposed at a first corner on a first end of the plurality of polymeric cover segments.

In addition or alternatively to any aspect discussed herein, the attachment portion of each of the plurality of polymeric cover segments is disposed at a middle portion on a first end of the plurality of polymeric cover segments.

In addition or alternatively to any aspect discussed herein, each corner of the first end of the plurality of cover segments is not directly attached to the expandable framework.

In addition or alternatively to any aspect discussed herein, each of the plurality of polymeric cover segments is configured to move circumferentially relative to an adjacent polymeric cover segment of the plurality of polymeric cover segments.

The above summary of some embodiments, aspects, and/or examples is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which.

Figure 1:
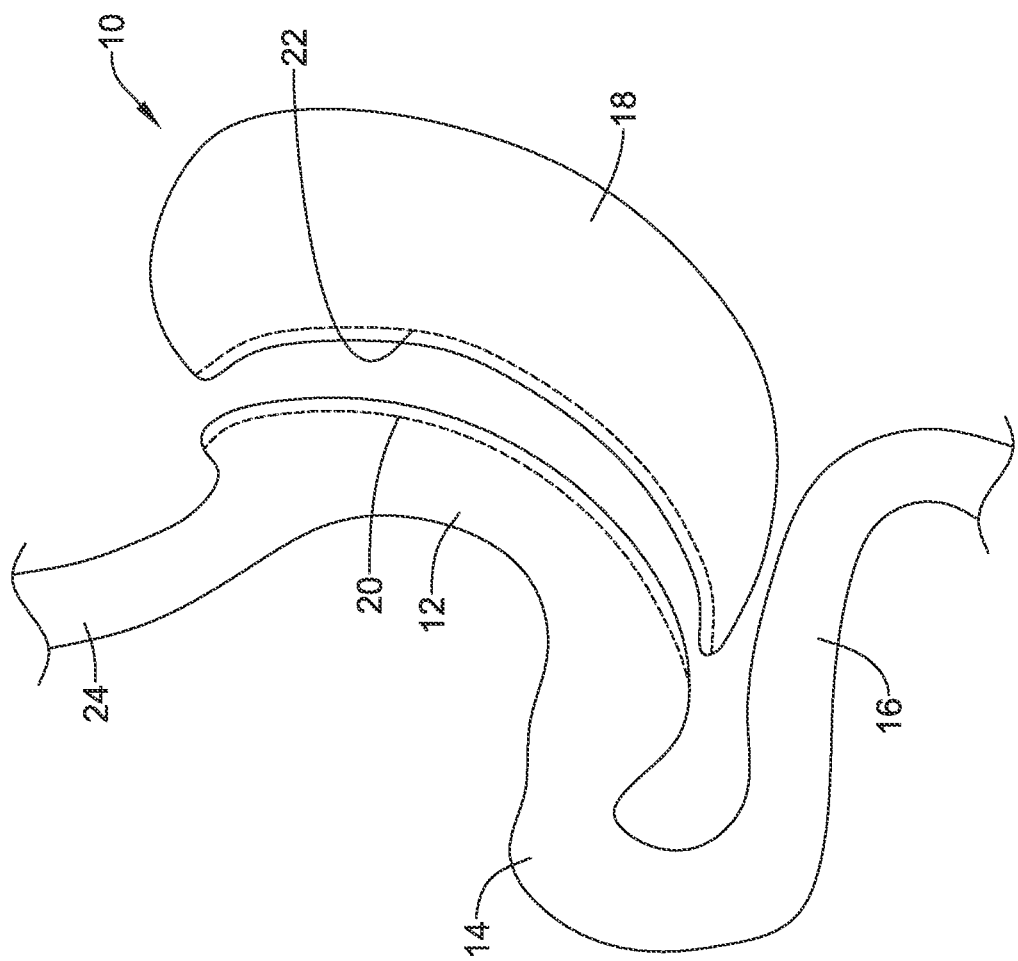
FIG. 1 is a schematic illustration of a gastric sleeve procedure.

While aspects of the disclosure are amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

The following description should be read with reference to the drawings, which are not necessarily to scale, wherein like reference numerals indicate like elements throughout the several views. The detailed description and drawings are intended to illustrate but not limit the claimed invention. Those skilled in the art will recognize that the various elements described and/or shown may be arranged in various combinations and configurations without departing from the scope of the disclosure. The detailed description and drawings illustrate example embodiments of the claimed invention.

For the following defined terms, these definitions shall be applied, unless a different definition is given in the claims or elsewhere in this specification.

All numeric values are herein assumed to be modified by the term "about," whether or not explicitly indicated. The term "about", in the context of numeric values, generally refers to a range of numbers that one of skill in the art would consider equivalent to the recited value (e.g., having the same function or result). In many instances, the term "about" may include numbers that are rounded to the nearest significant figure. Other uses of the term "about" (e.g., in a context other than numeric values) may be assumed to have their ordinary and customary definition(s), as understood from and consistent with the context of the specification, unless otherwise specified.

The recitation of numerical ranges by endpoints includes all numbers within that range, including the endpoints (e.g., 1 to 5 includes 1, 1.5, 2, 2.75, 3, 3.80, 4, and 5).

Although some suitable dimensions, ranges, and/or values pertaining to various components, features and/or specifications are disclosed, one of skill in the art, incited by the present disclosure, would understand desired dimensions, ranges, and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise. It is to be noted that in order to facilitate understanding, certain features of the disclosure may be described in the singular, even though those features may be plural or recurring within the disclosed embodiment(s). Each instance of the features may include and/or be encompassed by the singular disclosure(s), unless expressly stated to the contrary. For simplicity and clarity purposes, not all elements of the disclosed invention are necessarily shown in each figure or discussed in detail below. However, it will be understood that the following discussion may apply equally to any and/or all of the components for which there are more than one, unless explicitly stated to the contrary. Additionally, not all instances of some elements or features may be shown in each figure for clarity.

Relative terms such as "proximal", "distal", "advance", "retract", variants thereof, and the like, may be generally considered with respect to the positioning, direction, and/or operation of various elements relative to a user/operator/ manipulator of the device, wherein "proximal" and "retract" indicate or refer to closer to or toward the user and "distal" and "advance" indicate or refer to farther from or away from the user. In some instances, the terms "proximal" and "distal" may be arbitrarily assigned in an effort to facilitate understanding of the disclosure, and such instances will be readily apparent to the skilled artisan. Other relative terms, such as "upstream", "downstream", "inflow", and "outflow" refer to a direction of fluid flow within a lumen, such as a body lumen, a blood vessel, or within a device. Still other relative terms, such as "axial", "circumferential", "longitudinal", "lateral", "radial", etc. and/or variants thereof generally refer to direction and/or orientation relative to a central longitudinal axis of the disclosed structure or device.

The term "extent" may be understood to mean a greatest measurement of a stated or identified dimension, unless the extent or dimension in question is preceded by or identified as a "minimum", which may be understood to mean a smallest measurement of the stated or identified dimension. For example, "outer extent" may be understood to mean an outer dimension, "radial extent" may be understood to mean a radial dimension, "longitudinal extent" may be understood to mean a longitudinal dimension, etc. Each instance of an "extent" may be different (e.g., axial, longitudinal, lateral, radial, circumferential, etc.) and will be apparent to the skilled person from the context of the individual usage. Generally, an "extent" may be considered a greatest possible dimension measured according to the intended usage, while a "minimum extent" may be considered a smallest possible dimension measured according to the intended usage. In some instances, an "extent" may generally be measured orthogonally within a plane and/or cross-section, but may be, as will be apparent from the particular context, measured differently—such as, but not limited to, angularly, radially, circumferentially (e.g., along an arc), etc.

The terms "monolithic" and "unitary" shall generally refer to an element or elements made from or consisting of a single structure or base unit/element. A monolithic and/or unitary element shall exclude structure and/or features made by assembling or otherwise joining multiple discrete structures or elements together.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to implement the particular feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

For the purpose of clarity, certain identifying numerical nomenclature (e.g., first, second, third, fourth, etc.) may be used throughout the description and/or claims to name and/or differentiate between various described and/or claimed features. It is to be understood that the numerical nomenclature is not intended to be limiting and is exemplary only. In some embodiments, alterations of and deviations from previously-used numerical nomenclature may be made in the interest of brevity and clarity. That is, a feature identified as a "first" element may later be referred to as a "second" element, a "third" element, etc. or may be omitted entirely, and/or a different feature may be referred to as the "first" element. The meaning and/or designation in each instance will be apparent to the skilled practitioner.

The figures illustrate selected components and/or arrangements of an endoprosthesis or stent. It should be noted that in any given figure, some features of the endoprosthesis or stent may not be shown, or may be shown schematically, for simplicity. Additional details regarding some of the components of the endoprosthesis or stent may be illustrated in other figures in greater detail. It is to be noted that in order to facilitate understanding, certain features of the disclosure may be described in the singular, even though those features may be plural or recurring within the disclosed embodiment(s). Each instance of the features may include and/or be encompassed by the singular disclosure(s), unless expressly stated to the contrary. For example, a reference to "the filament", "the cell", "the strut", or other features may be equally referred to all instances and quantities beyond one of said feature. As such, it will be understood that the following discussion may apply equally to any and/or all of the components for which there are more than one within the endoprosthesis or stent, unless explicitly stated to the contrary. Additionally, not all instances of some elements or features may be shown in each figure for clarity.

There are a number of conditions, diseases, and surgical interventions that may result in wounds such as a leak or an abscess within the gastrointestinal tract. In many cases, a surgical intervention may create a staple line or suture line within a portion of the gastrointestinal tract. An illustrative but non-limiting example of such a surgical intervention is bariatric surgery. In bariatric surgery, which may be performed as an open surgery or more commonly as a laparoscopic surgery, an obese patient's stomach is made substantially smaller. As a result, the patient may be able to lose weight, particularly if they follow corresponding dietary restrictions. There are several common bariatric techniques including sleeve gastrectomy and Roux-en-Y.

FIG. 1 illustrates the results of a sleeve gastrectomy, in which a large portion of a patient's stomach 10 is cut away. As a result, a relatively small attached portion 12 of the patient's stomach 10 remains fluidly coupled through the pylorus 14 with the small intestine 16. As can be seen in FIG. 1, a relatively large resected portion 18 of the patient's stomach 10 is resected, or cut away from the attached portion 12 of the patient's stomach 10 that remains as part of the patient's effective gastrointestinal tract and extends from the esophagus 24 to the small intestine 16 It will be appreciated that as a result of the resection, a large staple line 20 is formed along one side of the small portion 12 of the patient's stomach 10. In some instances, a corresponding long staple line 22 may be formed along one side of the resected portion 18 of the patient's stomach 10.

Figure 2:
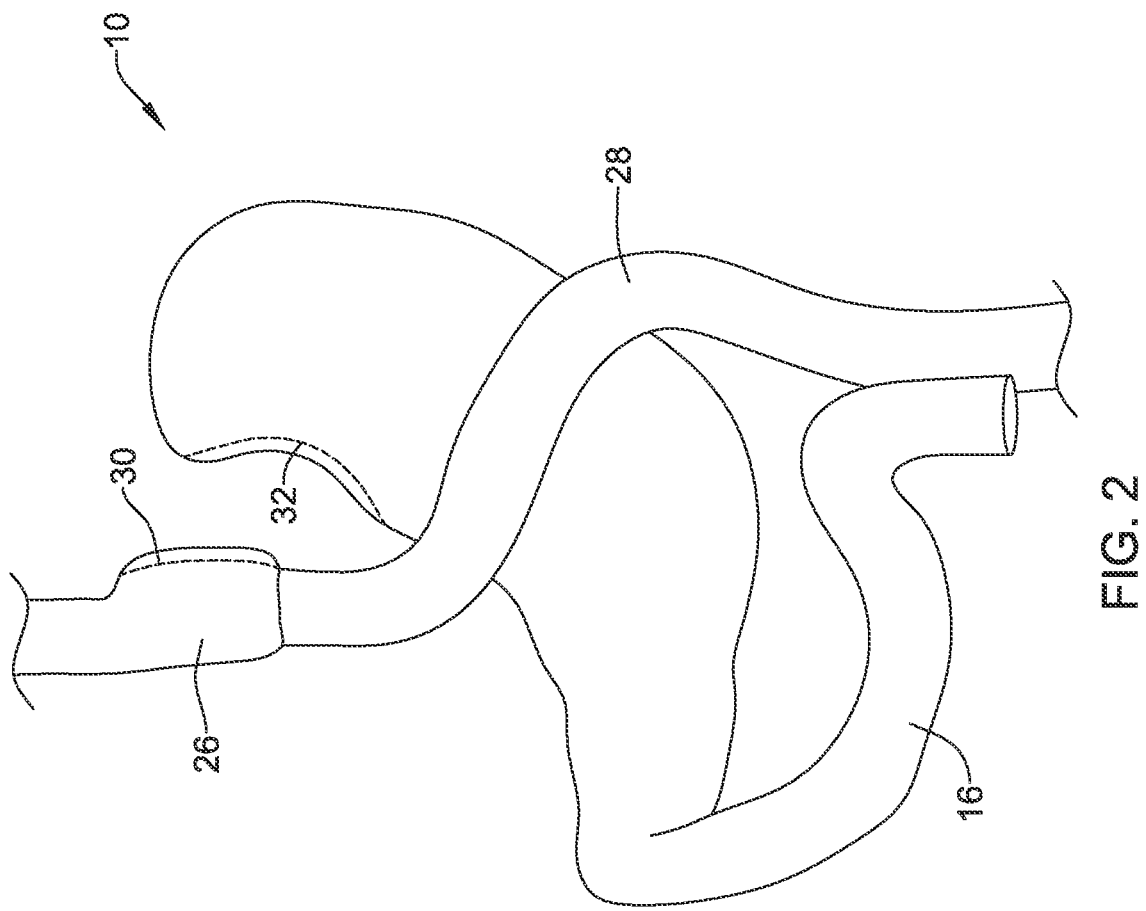
FIG. 2 is a schematic illustration of a Roux-en-Y procedure.

FIG. 2 illustrates the Roux-en-Y gastric bypass procedure in which an even larger portion of the patient's stomach 10 is resected and a portion of the small intestine 16 is also bypassed. In this procedure, a pouch 26 is formed from the very uppermost portion of the stomach 10 and is secured to the Roux limb 28, which is a portion of the small intestine 16 that is secured to the pouch 26. It will be appreciated that as a result of the resection, a staple line 30 is formed along one side of the pouch 26. A corresponding staple line 32 is formed along one side of the stomach 10.

It will be appreciated that leaks may occur along these staple lines, including the staple line 20 and the staple line 30. As a result, in some cases a pus-filled abscess may form adjacent the staple line 20 and/or the staple line 30. In some cases, it can be beneficial to place a stent, which in some cases may be a covered stent, proximate the wound in order to help seal off the leak, protect the wound from harsh stomach acids and keep nutritional contents such as food and beverages away from the wound. While leaks may occur along the staple line 22 and/or the staple line 32, it will be appreciated that this disclosure is directed to treating wounds that may be reached from inside the remaining gastrointestinal tract.

Figure 3:
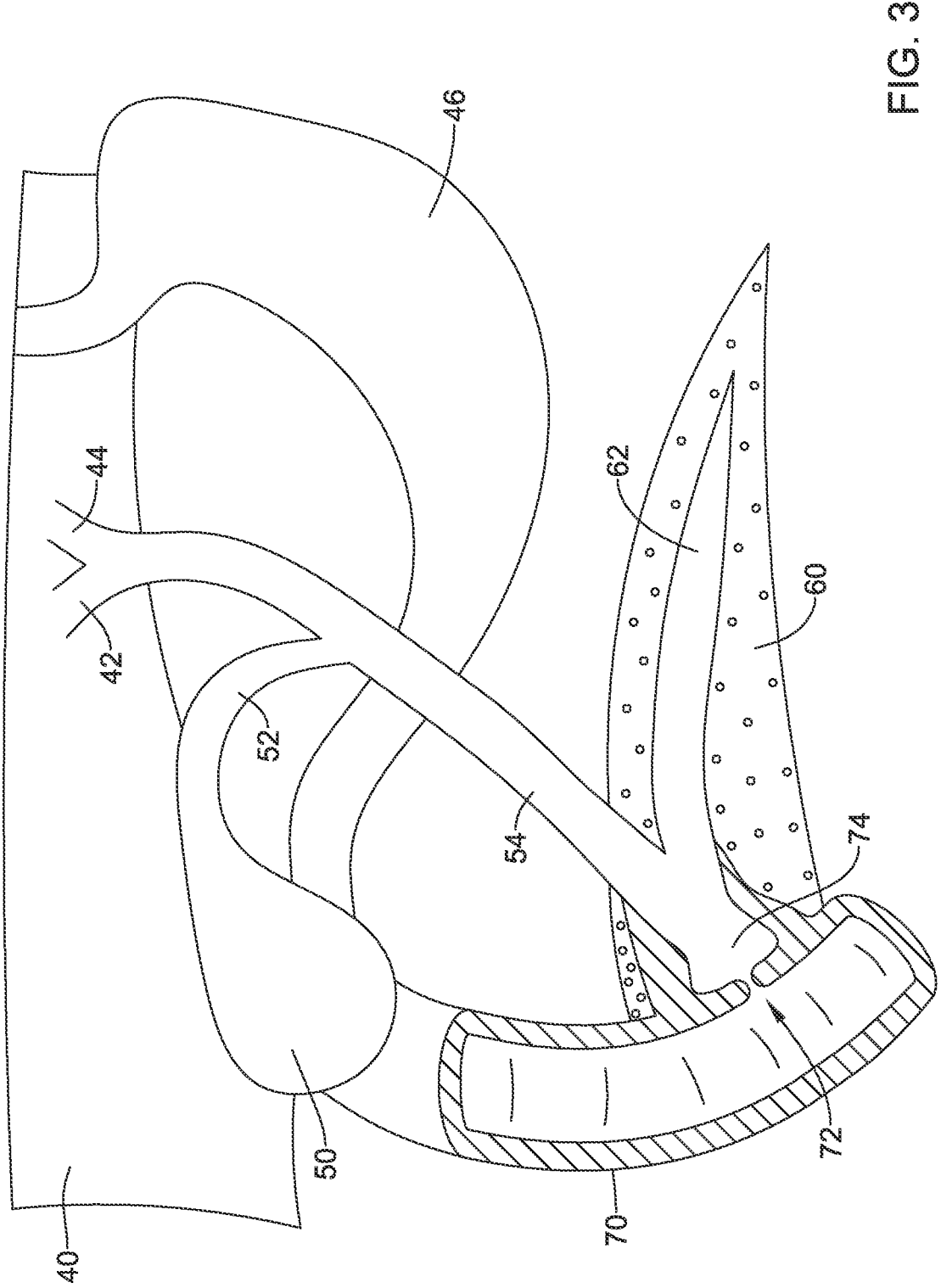
FIG. 3 illustrates aspects of a patient's biliary tree.

FIG. 3 illustrates selected features and relative positioning of a patient's anatomy related to the biliary tree, including the liver 40, the left hepatic duct 42, the right hepatic duct 44, the stomach 46, the gallbladder 50, the cystic duct 52, the common bile duct 54, the pancreas 60, the pancreatic duct 62, the duodenum 70 (shown partially cut away), the papilla of Vater 72, and the ampulla of Vater 74. In some patients, a stricture may form or develop that may partially or completely block a body lumen such as the common bile duct 54, the pancreatic duct 62, etc., thus requiring treatment. It will also be appreciated that this disclosure may be directed to features that facilitate and/or permit treatment of the biliary tree while also addressing wounds within the gastrointestinal tract.

Figure 4:
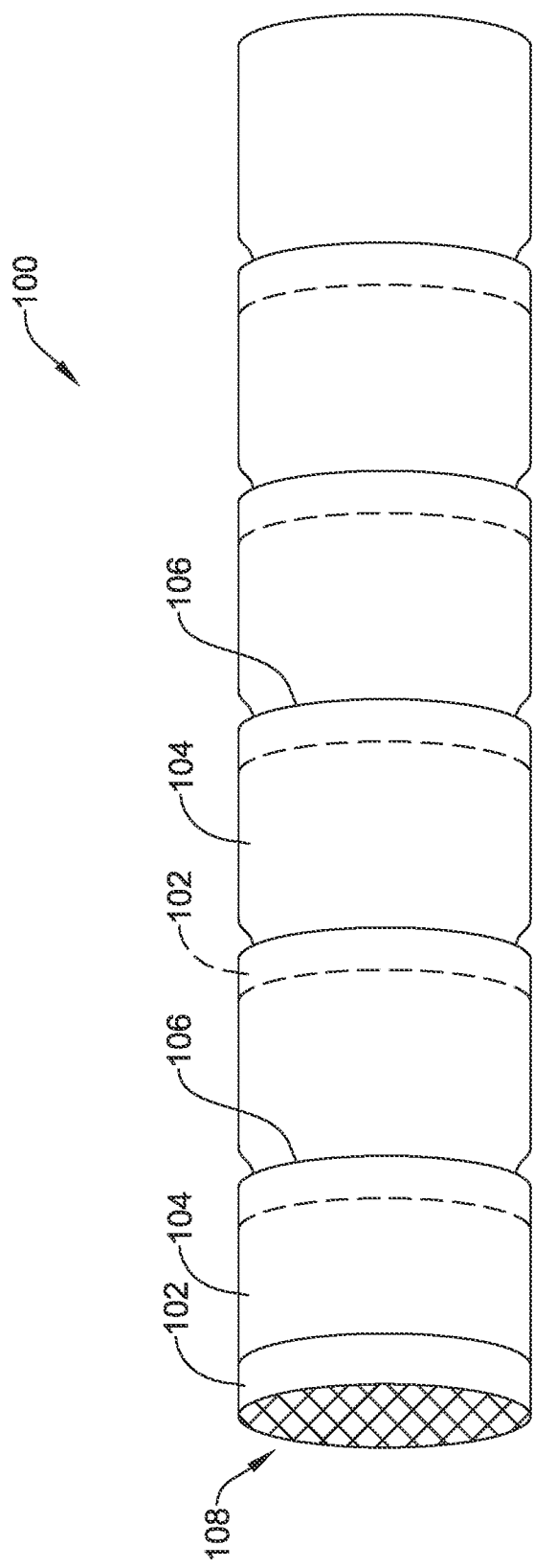
FIG. 4 illustrates an example endoprosthesis including a covering in a deployed configuration.
Figure 5:
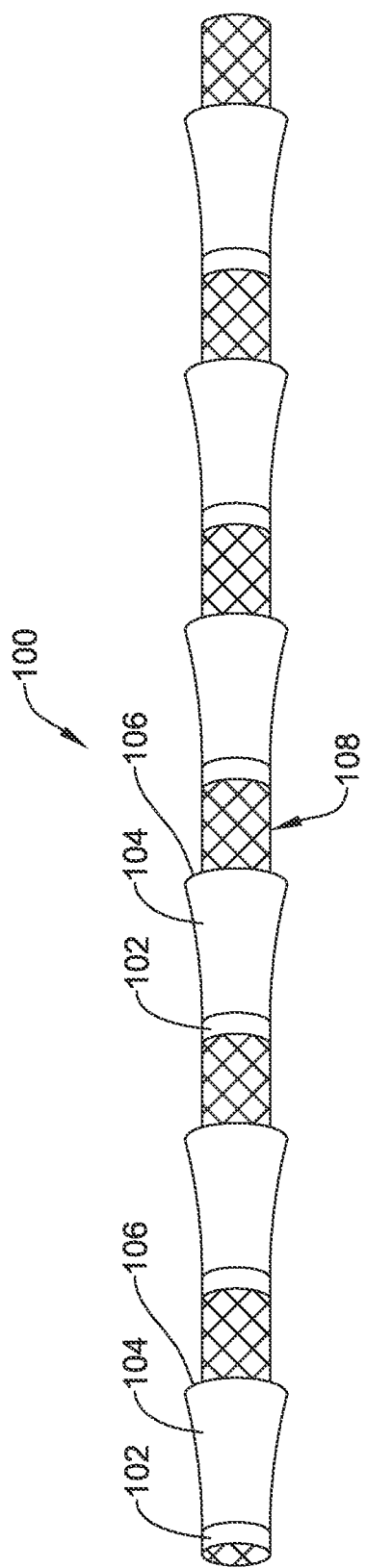
FIG. 5 illustrates the example endoprosthesis of FIG. 4 in a delivery configuration.

FIGS. 4 and 5 illustrate an example endoprosthesis 100 (which term may be used interchangeably with the term "stent" herein) comprising an expandable framework 108 extending axially from a first end, which may be considered a proximal end in some instances, to a second end, which may be considered a distal end in some instances, along a central longitudinal axis of the endoprosthesis 100 and/or the expandable framework 108. The endoprosthesis 100 and/or the expandable framework 108 may be configured to shift between a delivery configuration (e.g., FIG. 5) and a deployed configuration (e.g., FIG. 4). The delivery configuration may be a configuration in which the endoprosthesis 100 is axially elongated and/or radially collapsed or compressed compared to the deployed configuration. The deployed configuration may be a configuration in which the endoprosthesis 100 is axially shortened and/or radially expanded compared to the delivery configuration. In at least some embodiments, the endoprosthesis 100 and/or the expandable framework 108 may be self-expandable. For example, the endoprosthesis 100 and/or the expandable framework 108 may be formed from a shape memory material. In some embodiments, the endoprosthesis 100 and/or the expandable framework 108 may be mechanically expandable. For example, the endoprosthesis 100 and/or the expandable framework 108 may be expandable using an inflatable balloon, using an actuation member, or other suitable means. During delivery to a treatment site, the endoprosthesis 100 and/or the expandable framework 108 may be disposed within a lumen of a delivery sheath in the delivery configuration. Upon removal from the lumen of the delivery sheath, the endoprosthesis 100 and/or the expandable framework 108 may shift and/or may be shifted from the delivery configuration to the deployed configuration.

The expandable framework 108 may include and/or be formed with a plurality of cells. In some embodiments, the expandable framework 108 may include and/or be formed from one or more filaments interwoven around the central longitudinal axis of the endoprosthesis 100 and/or the expandable framework 108. In at least some embodiments, the one or more filaments may form and/or define the plurality of cells. In some embodiments, the expandable framework 108 may be braided, knitted, or woven from the one or more filaments. In some embodiments, the one or more filaments may be wires, threads, strands, etc. In some embodiments, adjacent filaments of the one or more filaments may define openings or interstices through a wall of the expandable framework 108. Alternatively, in some embodiments, the expandable framework 108 may be a monolithic structure formed from a cylindrical tubular member, such as a single, cylindrical laser-cut nickel-titanium (e.g., Nitinol) tubular member, in which the remaining (e.g., unremoved) portions of the tubular member form the stent struts and/or framework with openings or interstices defined therebetween.

The expandable framework 108 may be substantially tubular and/or may include a lumen extending axially therethrough along the central longitudinal axis of the expandable framework 108. In some embodiments, the expandable framework 108 may have an axial length of about 40 millimeters to about 250 millimeters, about 50 millimeters to about 225 millimeters, about 60 millimeters to about 200 millimeters, about 80 millimeters to about 175 millimeters, about 100 millimeters to about 150 millimeters, or another suitable range. In some embodiments, the expandable framework 108 may have a radial outer dimension or radial extent of about 5 millimeters to about 30 millimeters, about 6 millimeters to about 25 millimeters, about 8 millimeters to about 20 millimeters, about 10 millimeters to about 15 millimeters, or another suitable range. Other configurations are also contemplated. Some suitable but non-limiting materials for the endoprosthesis 100, the expandable framework 108, and/or components or elements thereof, for example metallic materials and/or polymeric materials, are described below.

The endoprosthesis 100 may include a covering comprising a plurality of polymeric cover segments 104 disposed on and/or about at least a portion of the expandable framework 108 and extending longitudinally along the expandable framework 108. Each polymeric cover segment 104 may be separate from and not directly attached to adjacent polymeric cover segments 104. Stated differently, each polymeric cover segment 104 may be separately formed and attached to the expandable framework 108 without direct attachment between adjacent polymeric cover segments 104. In some embodiments, the plurality of polymeric cover segments 104 may be disposed on and/or along an outer surface of the expandable framework 108. In some embodiments, the plurality of polymeric cover segments 104 may be impermeable to fluids, debris, medical instruments, etc. Some suitable but non-limiting materials for the plurality of polymeric cover segments 104, including but not limited to silicone, polyurethane, etc., are described below. Each of the plurality of polymeric cover segments 104 may include an attachment band 102 and a free end 106 opposite the attachment band 102. In some embodiments the attachment band 102 may be arranged at the distal end of a polymeric cover segment 104 and the free end 106 may be arranged at the proximal end of the polymer cover segment 104, opposite the attachment band 102. In other embodiments, the attachment band 102 may be arranged at the proximal end of the polymeric cover segment 104 and the free end 106 may be arranged at the distal end of the polymeric cover segment 104. In some embodiments, a portion of each of the plurality of polymeric cover segments 104 may be fixedly secured to, bonded to, or otherwise attached to a portion of the expandable framework 108 at and/or using its respective attachment band 102, while the remainder of the polymeric cover segment 104, including the free end 106 is not directly attached to (and thus free to move relative to) the expandable framework 108.

In some embodiments, the attachment band 102 may be fixedly secured to, bonded to, or otherwise attached intermittently about the circumference of the expandable framework 108. For example, the attachment band 102 may be discontinuously attached to the expandable framework 108. In some embodiments, the attachment band 102 may not necessarily be attached to the expandable framework 108 at each and every location the attachment band 102 touches the expandable framework 108. In some embodiments, the expandable framework 108 may be discontinuously embedded within the attachment band 102 of each of the plurality of polymeric cover segments 104.

In some embodiments, the attachment band 102 may be fixedly secured to, bonded to, or otherwise attached about the entire circumference of the expandable framework 108. For example, the attachment band 102 may be continuously attached to the expandable framework 108 about its entire length, width, and/or circumference. In some embodiments, anywhere the attachment band 102 touches the expandable framework 108, the attachment band 102 may be fixedly secured to, bonded to, or otherwise attached to the expandable framework 108. In some embodiments, the expandable framework 108 may be continuously embedded within the attachment band 102 of each of the plurality of polymeric cover segments 104.

Figure 6:
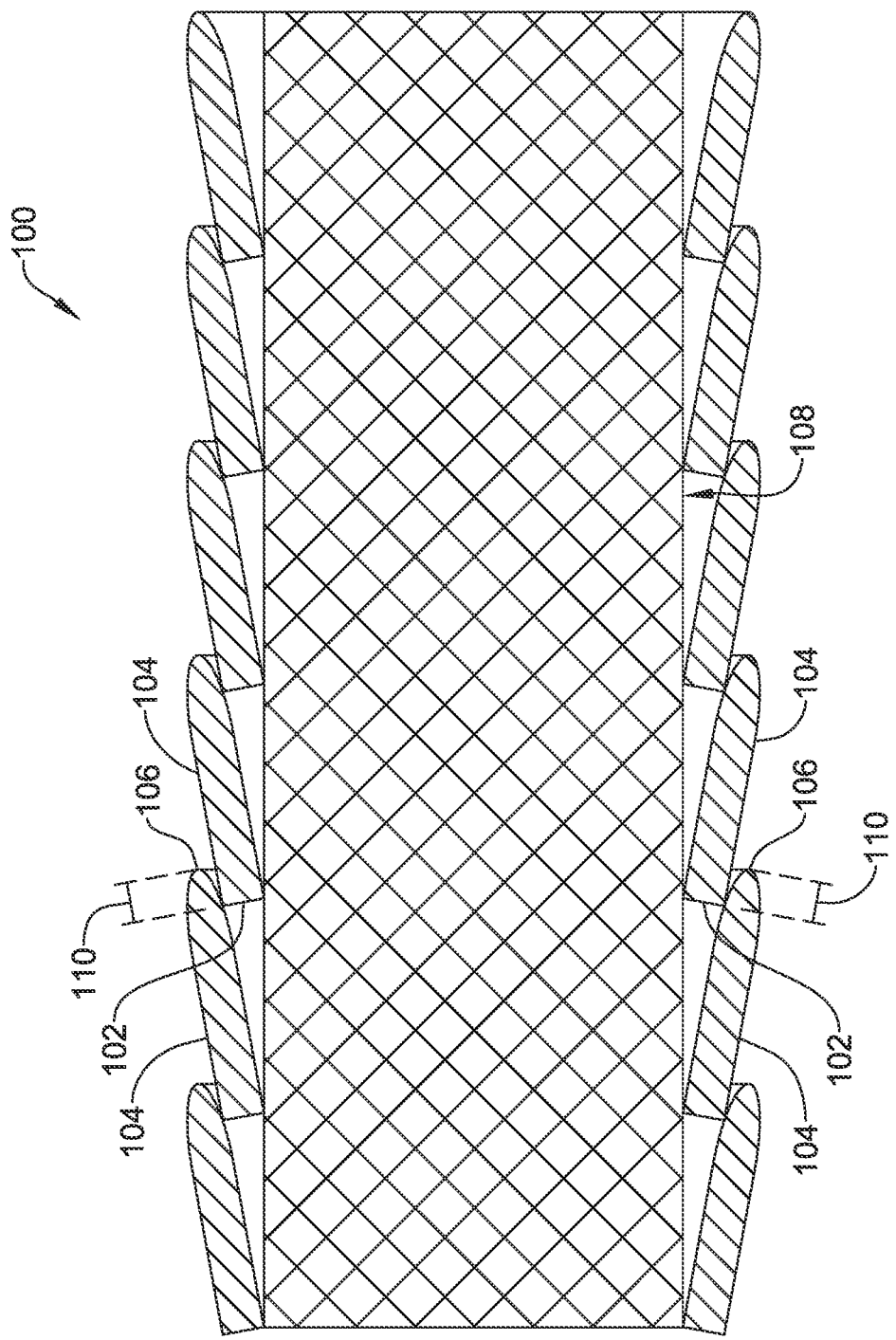
FIG. 6 is a partial cross-sectional view of the endoprosthesis of FIG. 4 in the expanded configuration when the endoprosthesis is substantially straight upon deployment.
Figure 7:
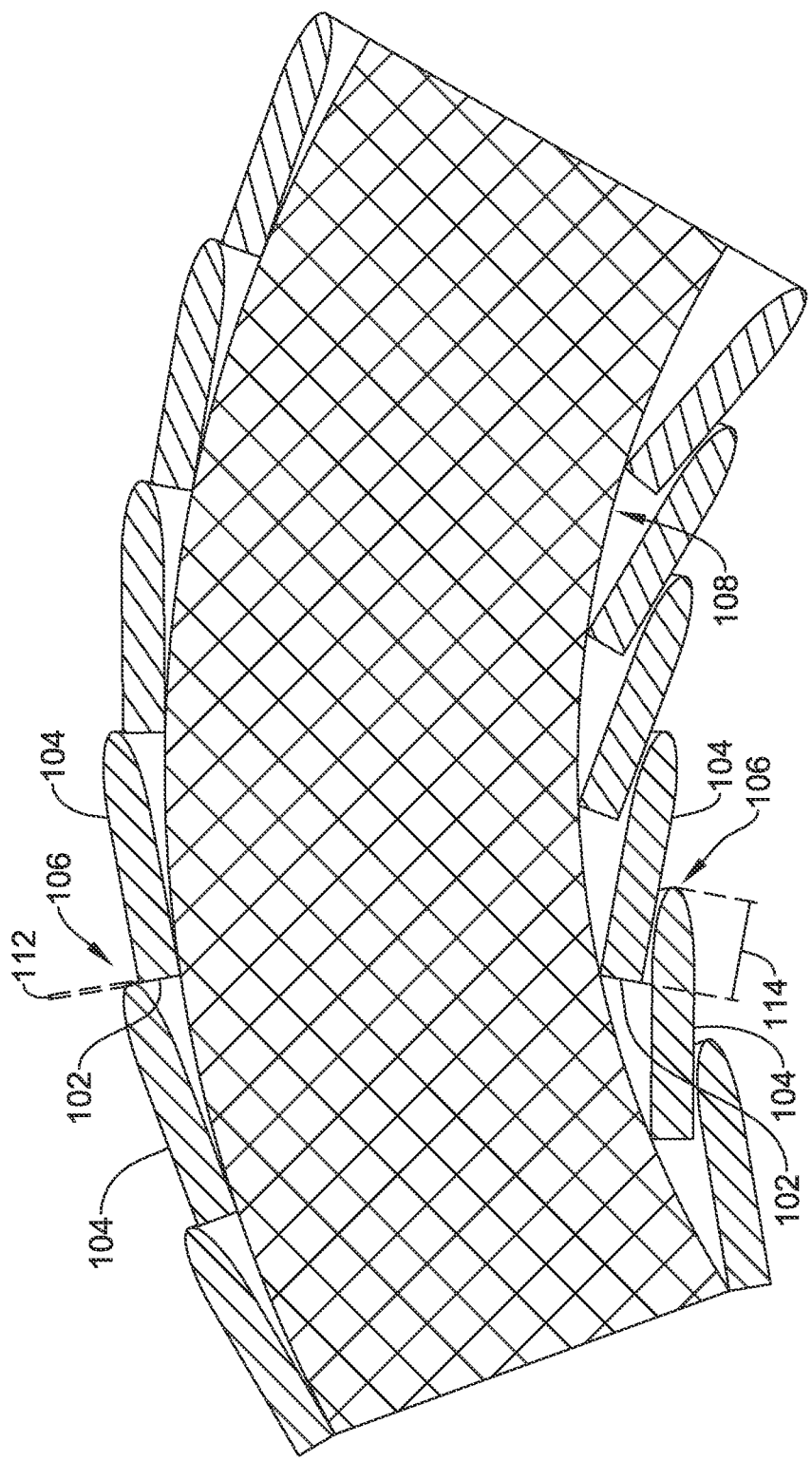
FIG. 7 is a partial cross-sectional view of the endoprosthesis of FIG. 4 in the expanded configuration when the endoprosthesis is curved or bent upon deployment.

In the delivery configuration in which the expandable framework 108 is longitudinally elongated and radially contracted, the plurality of polymeric cover segments 104 may be longitudinally and/or axially spaced apart from each other along the expandable framework 108, as seen in FIG. 5. Thus, the free end 106 of each of the plurality of cover segments 104 may be spaced away from and not overlap an adjacent cover segment 104 in the delivery configuration. In other words, the distal end of each cover segment 104 may be spaced proximally of a proximal end of an adjacent cover segment 104 located distally therefrom such that a portion of the expandable framework 108 is exposed and visible from the exterior of the endoprosthesis 100, or the proximal end of each cover segment 104 may be spaced distally of a distal end of an adjacent cover segment 104 located proximally therefrom such that a portion of the expandable framework 108 is exposed and visible from the exterior of the endoprosthesis 100. In the deployed configuration in which the expandable framework 108 is longitudinally contracted and radially expanded, the plurality of polymeric cover segments 104 may at least partially overlap each other in a longitudinal or axial direction as seen in FIGS. 4, 6, and 7, thus covering the portions of the expandable framework 108 exposed between adjacent cover segments 104 in the delivery configuration. For example, the free end 106 of each of the plurality of polymeric cover segments 104 may axially overlap, and may be disposed radially outward of, the attachment band 102 of an adjacent polymeric cover segment 104. In one example configuration, the attachment band 102 of each of the plurality of polymeric cover segments 104 may be oriented towards the first end (e.g., the proximal end) of the endoprosthesis 100 and/or the expandable framework 108 and the free end 106 of each of the plurality of polymeric cover segments 104 may extend from the attachment band 102 towards the second end (e.g., the distal end) of the endoprosthesis 100 and/or the expandable framework 108. However, in other embodiments, the attachment band 102 of each of the plurality of polymeric cover segments 104 may be oriented towards the second end (e.g., the distal end) of the endoprosthesis 100 and/or the expandable framework 108 and the free end 106 of each of the plurality of polymeric cover segments 104 may extend from the attachment band 102 towards the first end (e.g., the proximal end) of the endoprosthesis and/or the expandable framework 108.

In some embodiments, the covering and/or the plurality of polymeric cover segments 104 may extend along an entire length of the endoprosthesis 100 and/or the expandable framework 108. In some embodiments, the covering and/or the plurality of polymeric cover segments 104 may extend along a portion of the length of the endoprosthesis 100 and/or the expandable framework 108. In some embodiments, the covering and/or the plurality of polymeric cover segments 104 may extend discontinuously between the first end (e.g., the proximal end) of the endoprosthesis 100 and/or the expandable framework 108 and the second end (e.g., the distal end) of the endoprosthesis 100 and/or the expandable framework 108 in the delivery configuration. In some embodiments, the covering and/or the plurality of polymeric cover segments 104 may extend continuously from the first end (e.g., the proximal end) of the endoprosthesis 100 and/or the expandable framework 108 to the second end (e.g., the distal end) of the endoprosthesis 100 and/or the expandable framework 108 in the deployed configuration. In some embodiments, in the delivery configuration, at least some cells of the plurality of cells may be completely uncovered by the covering. In some embodiments, in the deployed configuration, all cells of the plurality of cells may be completely covered by the covering. Other configurations are also contemplated.

In one non-limiting example, the plurality of polymeric cover segments 104 may include a first polymeric cover segment, a second polymeric cover segment, and a third polymeric cover segment. Additional polymeric cover segments may also be included and/or other configurations are contemplated. The first polymeric cover segment may include a first attachment band and a first free end opposite the first attachment band. The second polymeric cover segment may include a second attachment band and a second free end opposite the second attachment band. The third polymeric cover segment may include a third attachment band and a third free end opposite the third attachment band. The first polymeric cover segment may be positioned over the expandable framework 108 adjacent the first end of the expandable framework 108 with the first attachment band oriented toward the first end of the expandable framework 108 and the first free end oriented toward the second end of the expandable framework 108. The second polymeric cover segment may be positioned over the expandable framework 108 adjacent the first polymeric cover segment with the second attachment band oriented toward the first end of the expandable framework 108 and the second free end oriented toward the second end of the expandable framework 108. The third polymeric cover segment may be positioned over the expandable framework 108 adjacent the second polymeric cover segment with the third attachment band oriented toward the first end of the expandable framework 108 and the third free end oriented toward the second end of the expandable framework 108.

In the delivery configuration, the first free end of the first polymeric cover segment may be longitudinally and/or axially spaced apart from the second attachment band of the second polymeric cover segment, and the second free end of the second polymeric cover segment may be longitudinally and/or axially spaced apart from the third attachment band of the third polymeric cover segment. In the deployed configuration, at least a portion of the first polymeric cover segment and/or the free end of first polymeric cover segment may longitudinally and/or axially overlap the second attachment band of the second polymeric cover segment, and at least a portion of the second polymeric cover segment and/or the free end of the second polymeric cover segment may longitudinally and/or axially overlap the third attachment band of the third polymeric cover segment. In the deployed configuration, the first free end of the first polymeric cover segment may be disposed radially outward of the second attachment band of the second polymeric cover segment, and the second free end of the second polymeric cover segment may be disposed radially outward of the third attachment band of the third polymeric cover segment. The arrangements and/or relative positioning described herein may be continued and/or replicated where additional polymeric cover segments are added or used in a particular configuration.

In use, when the endoprosthesis 100 is positioned within a body lumen with the endoprosthesis 100 and/or the expandable framework 108 in the deployed configuration, the plurality of polymeric cover segments 104 may be substantially pinched, squeezed, and/or compressed between the expandable framework 108 and the wall of the body lumen (not shown). In the deployed configuration, the plurality of polymeric cover segments 104 may form a substantially continuous outer covering disposed on and/or over the expandable framework 108, thereby forming a barrier, such as a sealed interface, between the lumen of the endoprosthesis 100 and/or the expandable framework 108 and the wall of the body lumen positioned radially outward of the outer covering and/or the plurality of polymeric cover segments 104. The plurality of polymeric cover segments 104 may isolate the lumen of the endoprosthesis 100 and/or the expandable framework 108 from the wall of the body lumen. The plurality of polymeric cover segments 104 may prevent tissue ingrowth into the lumen and/or the expandable framework 108 of the endoprosthesis 100 and thereby permit and/or aid removal of the endoprosthesis 100 and/or the expandable framework 108 from the body lumen.

FIG. 6 illustrates an example configuration of the plurality of polymeric cover segments 104 when the endoprosthesis 100 and/or the expandable framework 108 is deployed in a body lumen that is substantially straight. As may be seen in the figure, a longitudinal overlap 110 exists between the free end 106 of one polymeric cover segment 104 of the plurality of polymeric cover segments 104 and the attachment band 102 of an adjacent polymeric cover segment 104 of the plurality of polymeric cover segments 104. If referred to the above exemplary configuration, FIG. 6 illustrates the longitudinal overlap 110 between the second free end of the second polymeric cover segment and the third attachment band of the third polymeric cover segment, with the free end of the second polymeric cover segment positioned radially outward of the attachment band of the third polymeric cover segment. As may be also seen in FIG. 6, when the endoprosthesis 100 and/or the expandable framework 108 is deployed in a body lumen that is substantially straight (or if the endoprosthesis 100 and/or the expandable framework 108 is in the deployed configuration when not disposed within a body lumen), the longitudinal overlap 110 is substantially the same about an entire circumference of the endoprosthesis 100 and/or the expandable framework 108.

FIG. 7 illustrates an example configuration of the plurality of polymeric cover segments 104 when the endoprosthesis 100 and/or the expandable framework 108 is deployed in a body lumen that is curved or bent. As may be seen in the figure, an outside longitudinal overlap 112 exists between the free end 106 of one of the plurality of polymeric cover segments 104 and the attachment band 102 of an adjacent one of the plurality of polymeric cover segments 104, wherein the outside longitudinal overlap 112 is disposed at an outside of the curve or bend in the body lumen, and an inside longitudinal overlap 114 exists between the free end 106 of one of the plurality of polymeric cover segments 104 and the attachment band 102 of an adjacent one of the plurality of polymeric cover segments 104, wherein the inside longitudinal overlap 114 is disposed at an inside of the curve or bend in the body lumen. As may be clearly seen in FIG. 7, the outside longitudinal overlap 112 and the inside longitudinal overlap 114 may be different while maintaining a continuous overlap between adjacent polymeric cover segments 104 about the entire circumference of the endoprosthesis 100 and/or the expandable framework 108. If referred to the above exemplary configuration, FIG. 7 illustrates the outside longitudinal overlap 112 and the inside longitudinal overlap 114 between the second free end of the second polymeric cover segment and the third attachment band of the third polymeric cover segment.

In some embodiments, the inside longitudinal overlap 114 maybe generally constant and/or consistent along the length of the endoprosthesis 100, and the outside longitudinal overlap 112 may be generally constant and/or consistent along an entire length of the endoprosthesis 100. As such, the inside longitudinal overlap 114 and/or the outside longitudinal overlap 112 between a first pair of adjacent polymeric cover segments 104 may be similar to and/or identical to the inside longitudinal overlap 114 and/or the outside longitudinal overlap 112 between a second pair and/or a different pair of adjacent polymeric cover segments 104. In some embodiments, the inside longitudinal overlap 114 and/or the outside longitudinal overlap 112 may be variable along the length of the endoprosthesis 100. As such, the inside longitudinal overlap 114 and/or the outside longitudinal overlap 112 between a first pair of adjacent polymeric cover segments 104 may be different from the inside longitudinal overlap 114 and/or the outside longitudinal overlap 112 between a second pair and/or a different pair of adjacent polymeric cover segments 104.

Figure 8:
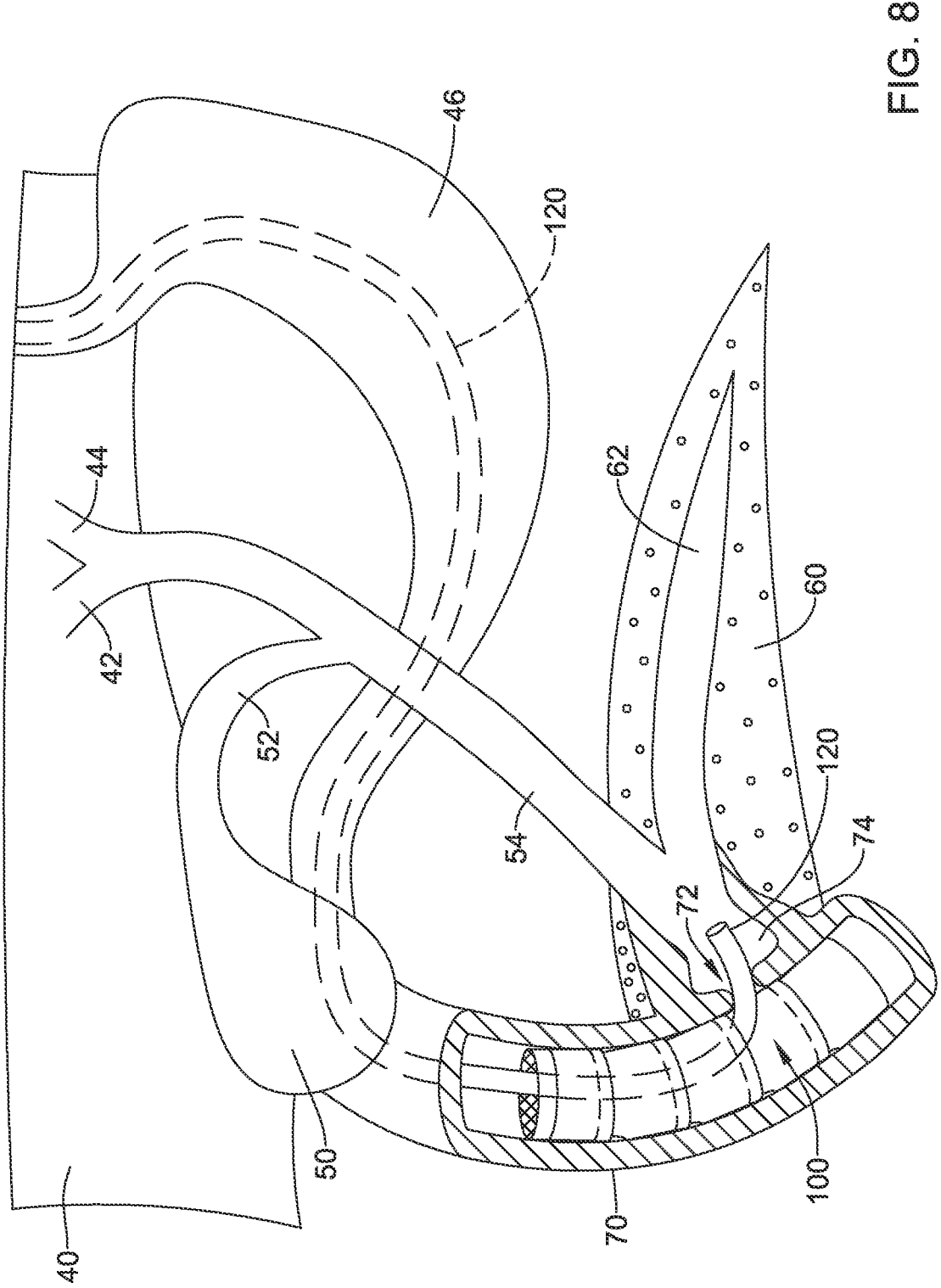
FIG. 8 illustrates an example placement of the endoprosthesis of FIGS. 4-7 in the patient's duodenum.

As may be appreciated, the configuration(s) of the endoprosthesis 100 disclosed herein may be beneficial when treating an adjacent and/or intersecting lumen, duct, and/or papilla. FIG. 8 illustrates one example configuration of the endoprosthesis 100 in use adjacent the papilla of Vater 72. In some embodiments, the endoprosthesis 100 may be placed within the duodenum 70 of the patient endoscopically, surgically, or using other suitable means. The endoprosthesis 100 may be located using an appropriate imaging technique to place the free end 106 of one or more of the plurality of polymeric cover segments 104 adjacent the intersecting lumen, duct, and/or papilla (e.g., the papilla of Vater 72, etc.). This may permit a clinician to advance a treatment device 120 (e.g., a catheter, an endoscope, etc.) through the lumen of the endoprosthesis 100 and/or the expandable framework 108, through the wall of the expandable framework 108, and/or between adjacent polymeric cover segments 104 and into the intersecting lumen, duct, and/or papilla (e.g., the papilla of Vater 72, etc.). In some embodiments, the expandable framework 108 may be formed with an access opening through the wall of the expandable framework 108 (e.g., an enlarged cell or cells, adjacent filaments having greater spacing apart from each other, one or more filament segments cut away within a portion of the wall, etc.) adjacent the free end 106 of one or more of the plurality of polymeric cover segments 104 to permit the passage of a medical device and/or the treatment device 120 therethrough.

In the illustrated example, the treatment device 120 passes between the free end 106 of the third polymeric cover segment and the attachment band 102 of the fourth polymeric cover segment. Other configurations and/or arrangements are also contemplated. Thereafter, the treatment device 120 may be used to deliver a medicament or another treatment device within the intersecting lumen (e.g., the ampulla of Vater 74, etc.), duct (e.g., the common bile duct 54, the pancreatic duct 62, etc.), and/or papilla (e.g., the papilla of Vater 72, etc.). The disclosed configuration(s) may permit the use and/or placement of a covered endoprosthesis 100 within the duodenum 70 for the desired treatment(s) thereof, while also permitting access to and/or treatment of the intersecting lumen, duct, and/or papilla.

Figure 9:
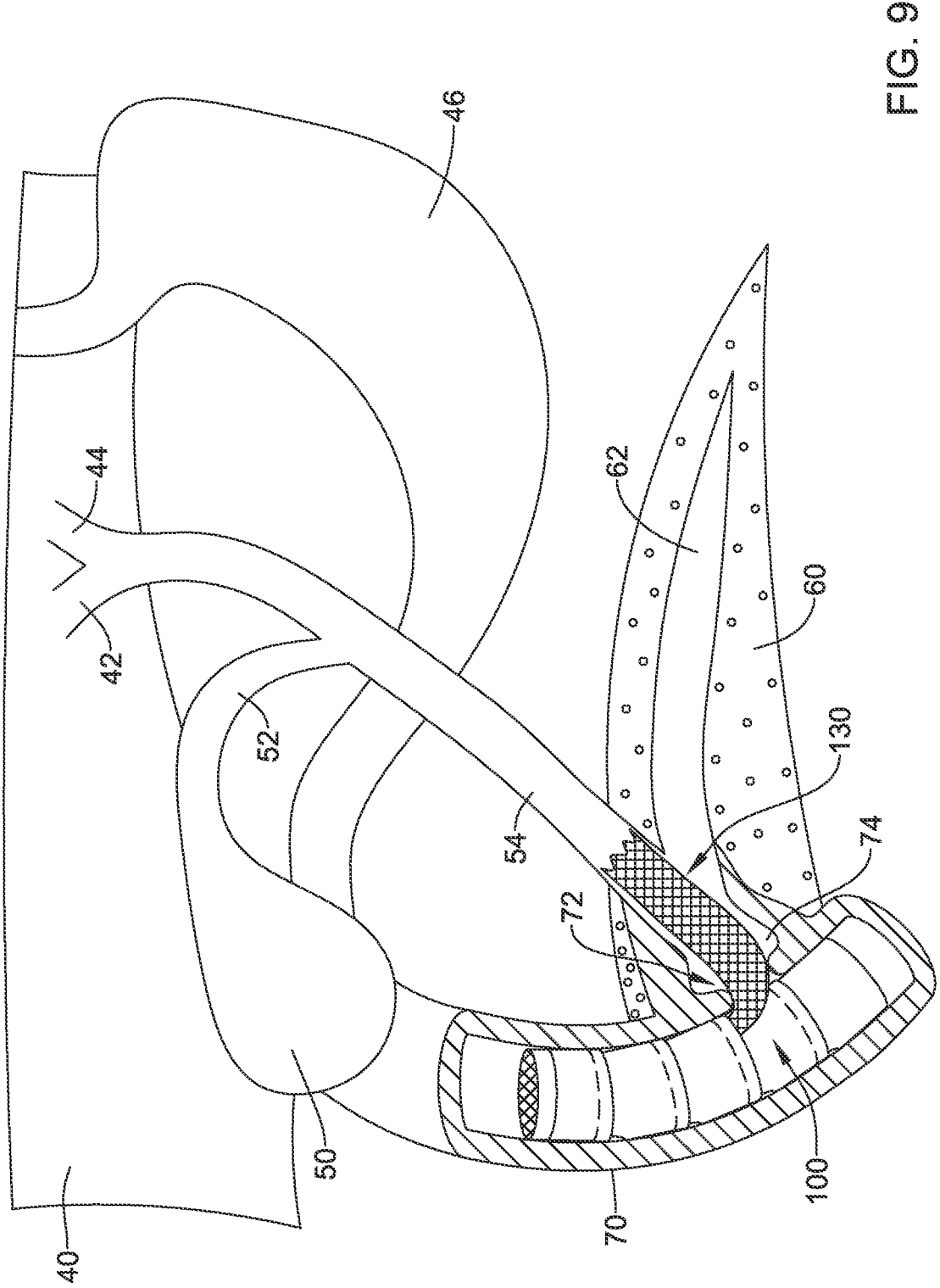
FIG. 9 illustrates an example placement of the endoprosthesis of FIGS. 4-7 in the patient's duodenum.

FIG. 9 illustrates another example configuration of the endoprosthesis 100 in use adjacent the papilla of Vater 72. In some embodiments, the endoprosthesis 100 may be placed within the duodenum 70 of the patient endoscopically, surgically, or using other suitable means. The endoprosthesis 100 may be located using an appropriate imaging technique to place the free end 106 of one or more of the plurality of polymeric cover segments 104 adjacent the intersecting lumen, duct, and/or papilla (e.g., the papilla of Vater 72, etc.). This may permit a clinician to advance a stent 130 through the lumen of the endoprosthesis 100 and/or the expandable framework 108, through the wall of the expandable framework 108, and/or between adjacent polymeric cover segments 104 and into the intersecting lumen, duct, and/or papilla (e.g., the papilla of Vater 72, etc.). In one example, the stent 130 may be configured to dilate the intersecting lumen, duct, and/or papilla in an expanded and/or deployed configuration to maintain and/or re-establish patency therethrough. In at least some embodiments, the stent 130 may be configured to exert a radially outward force upon a wall of the intersecting lumen, duct, and/or papilla. In some embodiments, the expandable framework 108 may be formed with an access opening through the wall of the expandable framework 108 (e.g., an enlarged cell or cells, adjacent filaments having greater spacing apart from each other, one or more filament segments cut away within a portion of the wall, etc.) adjacent the free end 106 of one or more of the plurality of polymeric cover segments 104 to permit the passage of a medical device and/or the stent 130 therethrough.

In the illustrated example, the stent 130 passes between the free end 106 of the third polymeric cover segment and the attachment band 102 of the fourth polymeric cover segment. Other configurations and/or arrangements are also contemplated. Thereafter, the stent 130 may be enlarged within the intersecting lumen (e.g., the ampulla of Vater 74, etc.), duct (e.g., the common bile duct 54, the pancreatic duct 62, etc.), and/or papilla (e.g., the papilla of Vater 72, etc.). In some embodiments, the stent 130 may be a bare stent, a partially covered stent, or a fully covered stent. In some embodiments, the stent 130 may be securable and/or attachable to the expandable framework 108 to form a bifurcated stent system. The bifurcated stent system may be usable in any body lumen where treatment using a covered endoprosthesis in the primary/main body lumen is indicated. The disclosed configuration(s) may permit the use and/or placement of a covered endoprosthesis 100 within the duodenum 70 for the desired treatment(s) thereof, while also permitting access to and/or treatment of the intersecting lumen, duct, and/or papilla.

Figure 10:
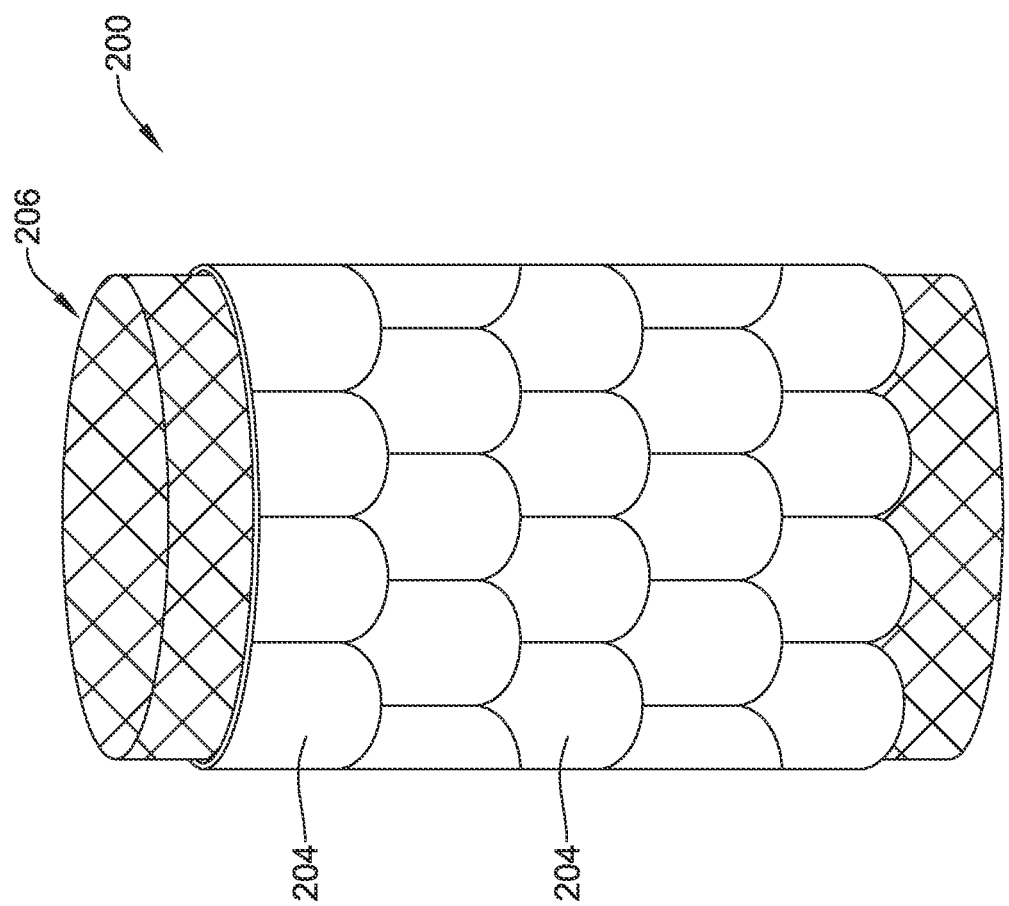
FIG. 10 illustrates an alternative configuration of the endoprosthesis of FIG. 4 including a covering.

FIG. 10 illustrates an alternative configuration of an endoprosthesis 200. The endoprosthesis 200 may include an expandable framework 206 extending axially from a first end, which may be considered a proximal end in some instances, to a second end, which may be considered a distal end in some instances, along a central longitudinal axis of the endoprosthesis 200 and/or the expandable framework 206. The endoprosthesis 200 and/or the expandable framework 206 may be configured to shift between a delivery configuration and a deployed configuration. The delivery configuration may be axially elongated and/or radially collapsed or compressed compared to the deployed configuration. The deployed configuration may be axially shortened and/or radially expanded compared to the delivery configuration. In at least some embodiments, the endoprosthesis 200 and/or the expandable framework 206 may be self-expandable. For example, the endoprosthesis 200 and/or the expandable framework 206 may be formed from a shape memory material. In some embodiments, the endoprosthesis 200 and/or the expandable framework 206 may be mechanically expandable. For example, the endoprosthesis 200 and/or the expandable framework 206 may be expandable using an inflatable balloon, using an actuation member, or other suitable means. During delivery to a treatment site, the endoprosthesis 200 and/or the expandable framework 206 may be disposed within a lumen of a delivery sheath in the delivery configuration. Upon removal from the lumen of the delivery sheath, the endoprosthesis 200 and/or the expandable framework 206 may shift and/or may be shifted from the delivery configuration to the deployed configuration.

The expandable framework 206 may include and/or be formed with a plurality of cells. In some embodiments, the expandable framework 206 may include and/or be formed from one or more filaments interwoven around the central longitudinal axis of the endoprosthesis 200 and/or the expandable framework 206. In at least some embodiments, the one or more filaments may form and/or define the plurality of cells. In some embodiments, the expandable framework 206 may be braided, knitted, or woven from the one or more filaments. In some embodiments, the one or more filaments may be wires, threads, strands, etc. In some embodiments, adjacent filaments of the one or more filaments may define openings or interstices through a wall of the expandable framework 206. Alternatively, in some embodiments, the expandable framework 206 may be a monolithic structure formed from a cylindrical tubular member, such as a single, cylindrical laser-cut nickel-titanium (e.g., Nitinol) tubular member, in which the remaining (e.g., unremoved) portions of the tubular member form the stent struts and/or framework with openings or interstices defined therebetween.

The expandable framework 206 may be substantially tubular and/or may include a lumen extending axially therethrough along the central longitudinal axis. In some embodiments, the expandable framework 206 may have an axial length of about 40 millimeters to about 250 millimeters, about 50 millimeters to about 225 millimeters, about 60 millimeters to about 200 millimeters, about 80 millimeters to about 175 millimeters, about 100 millimeters to about 150 millimeters, or another suitable range. In some embodiments, the expandable framework 206 may have a radial outer dimension or radial extent of about 5 millimeters to about 30 millimeters, about 6 millimeters to about 25 millimeters, about 8 millimeters to about 20 millimeters, about 10 millimeters to about 15 millimeters, or another suitable range. Other configurations are also contemplated. Some suitable but non-limiting materials for the endoprosthesis 200, the expandable framework 206, and/or components or elements thereof, for example metallic materials and/or polymeric materials, are described below.

The endoprosthesis 200 may include a covering comprising a plurality of polymeric cover segments 204 disposed on and/or about at least a portion of the expandable framework 206. In some embodiments, the plurality of polymeric cover segments 204 may be disposed on and/or along an outer surface of the expandable framework 206. In some embodiments, the plurality of polymeric cover segments 204 may be impermeable to fluids, debris, medical instruments, etc. Some suitable but non-limiting materials for the plurality of polymeric cover segments 204, including but not limited to silicone, polyurethane, etc., are described below. Each of the plurality of polymeric cover segments 204 may include an attachment portion and a free end opposite the attachment portion. In some embodiments, each of the plurality of polymeric cover segments 204 may be fixedly secured to, bonded to, or otherwise attached to a portion of the expandable framework 206 at and/or using its respective attachment portion. In some embodiments, none of the plurality of polymeric cover segments 204 is directly attached to another polymeric cover segment of the plurality of polymeric cover segments 204.

In some embodiments, the attachment portion may be fixedly secured to, bonded to, or otherwise attached intermittently about the circumference of the expandable framework 206. For example, the attachment portion may be discontinuously attached to the expandable framework 206. In some embodiments, the attachment portion may not necessarily be attached to the expandable framework 206 at each and every location the attachment portion touches the expandable framework 206. In some embodiments, the expandable framework 206 may be discontinuously embedded within the attachment portion of each of the plurality of polymeric cover segments 204.

In some embodiments, the plurality of polymeric cover segments 204 may be arranged like and/or may move relative to each other similar to fish scales. The plurality of polymeric cover segments 204 may be configured to overlap each other longitudinally and/or circumferentially. In some embodiments, adjacent rows of the plurality of polymeric cover segments 204 may be configured to move longitudinally relative to each other. In some embodiments, individual polymeric cover segments within a row or rows of the plurality of polymeric cover segments 204 may be configured to move longitudinally relative to each other and/or relative to an adjacent polymeric cover segment of the plurality of polymeric cover segments 204. In some embodiments, adjacent rows of the plurality of polymeric cover segments 204 may be configured to move circumferentially relative to each other. In some embodiments, individual polymeric cover segments within a row or rows of the plurality of polymeric cover segments 204 may be configured to move circumferentially relative to each other and/or relative to an adjacent polymeric cover segment of the plurality of polymeric cover segments 204. In some embodiments, each of the plurality of polymeric cover segments 204 may be configured to move both longitudinally and circumferentially relative to each other and/or relative to an adjacent polymeric cover segment of the plurality of polymeric cover segments 204.

In some embodiments, the attachment portion may be disposed at a first corner on a first end of the plurality of polymeric cover segments 204 opposite a free end (e.g., a second end) of the plurality of polymeric cover segments 204, wherein a second corner on the first end of the plurality of polymeric cover segments 204 is unattached (e.g., not directly attached) to the expandable framework 206. In some embodiments, the plurality of polymeric cover segments 204 within a particular row or column of the plurality of polymeric cover segments 204 may be configured to overlap each other and move relative to each other in one circumferential direction. In some embodiments, the attachment portion may be disposed at a middle portion on the first end of the plurality of polymeric cover segments 204 opposite the free end (e.g., the second end), wherein each corner on the first end of the plurality of polymeric cover segments 204 is unattached (e.g., not directly attached) to the expandable framework 206. In some embodiments, the plurality of polymeric cover segments 204 within a particular row or column of the plurality of polymeric cover segments 204 may be configured to overlap each other and move relative to each other in one or both circumferential directions.

Figure 11:
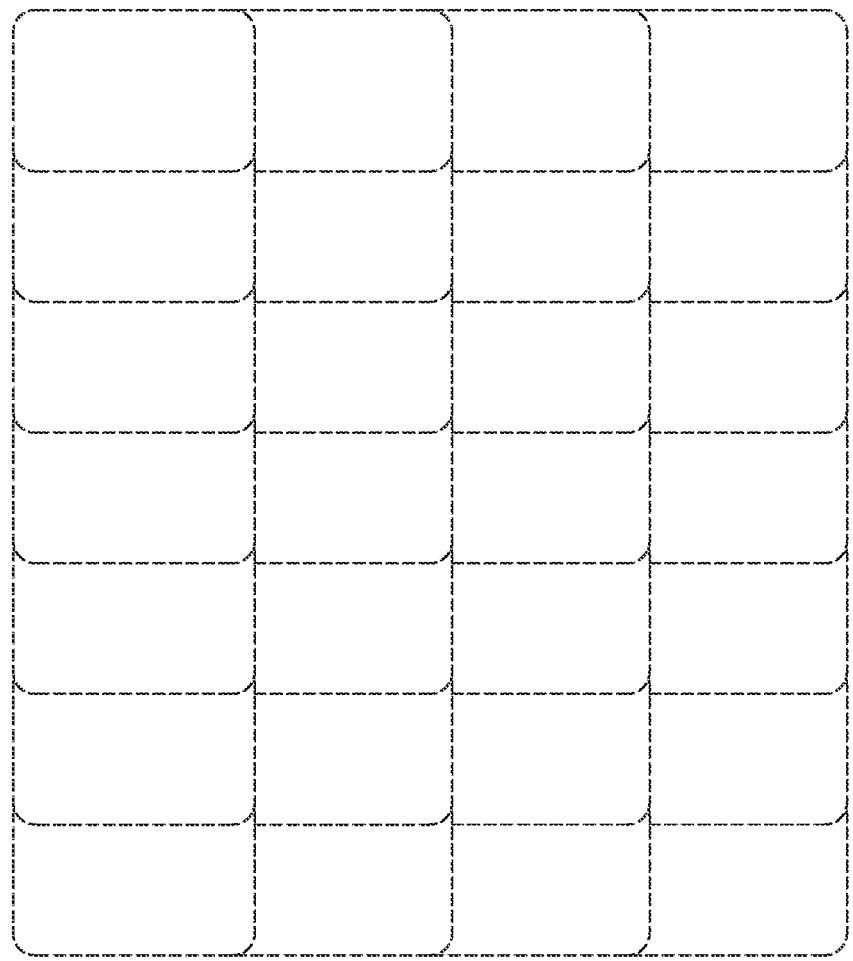
FIG. 11 illustrates an example configuration of the covering of the endoprosthesis of FIG. 10.
Figure 12:
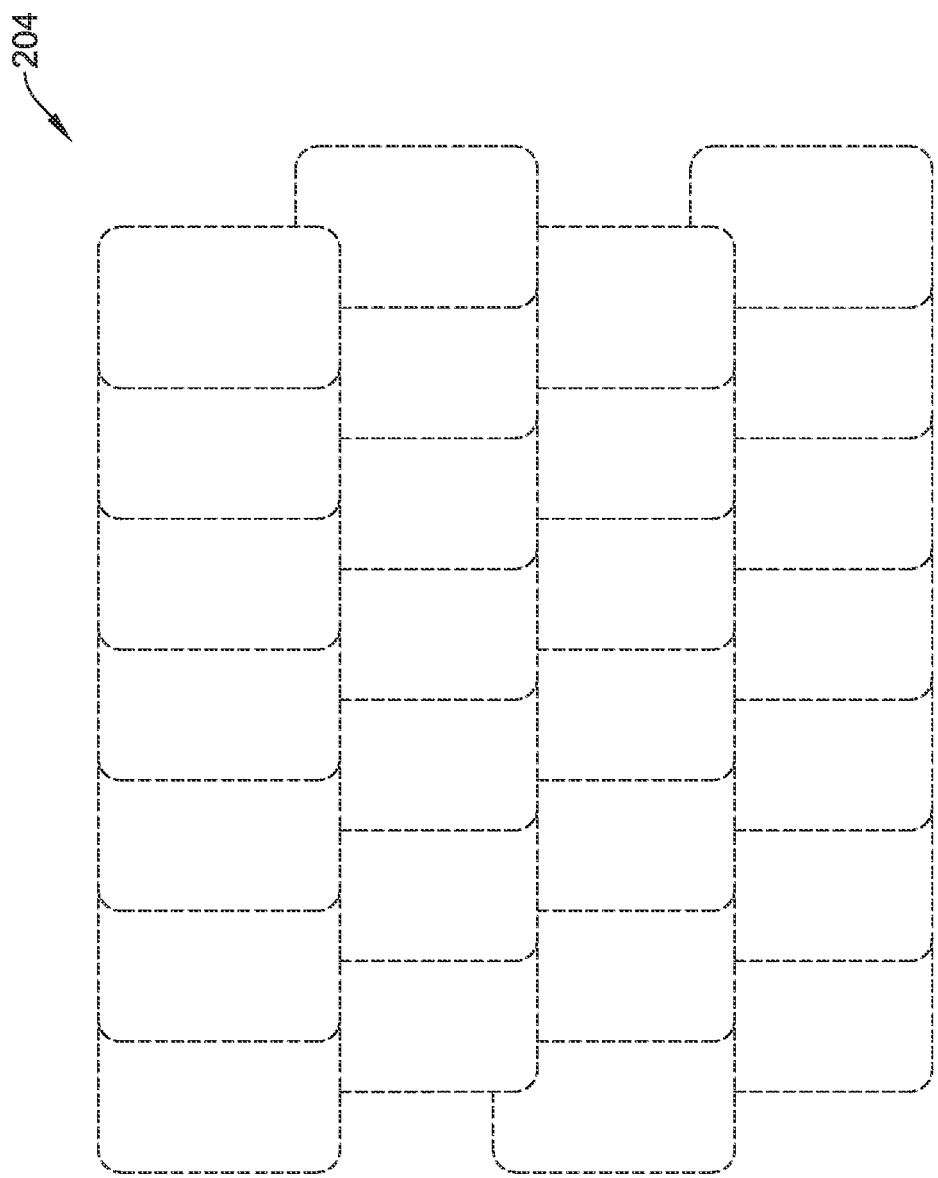
FIG. 12 illustrates an example configuration of the covering of the endoprosthesis of FIG. 10.

In some embodiments, the plurality of polymeric cover segments 204 may be arranged in formal rows and/or columns, as shown in FIG. 11 for example. In some embodiments, the plurality of polymeric cover segments 204 may be arranged with a circumferential offset between adjacent rows, as shown in FIG. 12 for example. A sealing effect may be maintained by the degree of overlap between individual cover segments within a row and between cover segments of adjacent rows. In some embodiments, the attachment portion of the plurality of polymeric cover segments 204 may be directly attached to a polymer backing strip. In one example, during manufacturing the plurality of polymeric cover segments 204 may be formed into rows in a flat arrangement, which may later be formed around and attached to the expandable framework 206. Other configurations are also contemplated.

The materials that can be used for the various components of the endoprosthesis 100/200 and the various elements thereof disclosed herein may include those commonly associated with medical devices. For simplicity purposes, the following discussion makes reference to the endoprosthesis 100/200. However, this is not intended to limit the devices and methods described herein, as the discussion may be applied to other elements, members, components, or devices disclosed herein, such as, but not limited to, the expandable framework, the anchoring portion, the body portion, the linking portion, the polymeric cover, and/or elements or components thereof.

In some embodiments, the endoprosthesis 100/200, and/or components thereof, may be made from a metal, metal alloy, polymer (some examples of which are disclosed below), a metal-polymer composite, ceramics, combinations thereof, and the like, or other suitable material.

Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, polyurethane silicone copolymers (for example, ElastEon® from Aortech Biomaterials or ChronoSil® from AdvanSource Biomaterials), biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; platinum; palladium; gold; combinations thereof; or any other suitable material.

In some embodiments, a linear elastic and/or non-superelastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, portions or all of the endoprosthesis 100/200, and/or components thereof, may also be doped with, made of, or otherwise include a radiopaque material. Radiopaque materials are understood to be materials capable of producing a relatively bright image on a fluoroscopy screen or another imaging technique during a medical procedure. This relatively bright image aids the user of the endoprosthesis 100/200 in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the endoprosthesis 100/200 to achieve the same result.

In some embodiments, a degree of Magnetic Resonance Imaging (MRI) compatibility is imparted into the endoprosthesis 100/200 and/or other elements disclosed herein. For example, the endoprosthesis 100/200, and/or components or portions thereof, may be made of a material that does not substantially distort the image and create substantial artifacts (i.e., gaps in the image). Certain ferromagnetic materials, for example, may not be suitable because they may create artifacts in an MRI image. The endoprosthesis 100/200, or portions thereof, may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

In some embodiments, the endoprosthesis 100/200 and/or other elements disclosed herein may include a fabric material disposed over or within the structure. The fabric material may be composed of a biocompatible material, such a polymeric material or biomaterial, adapted to promote tissue ingrowth. In some embodiments, the fabric material may include a bioabsorbable material. Some examples of suitable fabric materials include, but are not limited to, polyethylene glycol (PEG), nylon, polytetrafluoroethylene (PTFE, ePTFE), a polyolefinic material such as a polyethylene, a polypropylene, polyester, polyurethane, and/or blends or combinations thereof.

In some embodiments, the endoprosthesis 100/200 and/or other elements disclosed herein may include and/or be formed from a textile material. Some examples of suitable textile materials may include synthetic yarns that may be flat, shaped, twisted, textured, pre-shrunk or un-shrunk. Synthetic biocompatible yarns suitable for use in the present invention include, but are not limited to, polyesters, including polyethylene terephthalate (PET) polyesters, polypropylenes, polyethylenes, polyurethanes, polyolefins, polyvinyls, polymethylacetates, polyamides, naphthalene dicarboxylene derivatives, natural silk, and polytetrafluoroethylenes. Moreover, at least one of the synthetic yarns may be a metallic yarn or a glass or ceramic yarn or fiber. Useful metallic yarns include those yarns made from or containing stainless steel, platinum, gold, titanium, tantalum, or a Ni—Co—Cr-based alloy. The yarns may further include carbon, glass, or ceramic fibers. Desirably, the yarns are made from thermoplastic materials including, but not limited to, polyesters, polypropylenes, polyethylenes, polyurethanes, polynaphthalenes, polytetrafluoroethylenes, and the like. The yarns may be of the multifilament, monofilament, or spun-types. The type and denier of the yarn chosen may be selected in a manner which forms a biocompatible and implantable prosthesis and, more particularly, a vascular structure having desirable properties.

In some embodiments, the endoprosthesis 100/200 and/or other elements disclosed herein may include and/or be treated with a suitable therapeutic agent. Some examples of suitable therapeutic agents may include anti-thrombogenic agents (such as heparin, heparin derivatives, urokinase, and PPack (dextrophenylalanine proline arginine chloromethylketone)); anti-proliferative agents (such as enoxaparin, angiopeptin, monoclonal antibodies capable of blocking smooth muscle cell proliferation, hirudin, and acetylsalicylic acid); anti-inflammatory agents (such as dexamethasone, prednisolone, corticosterone, budesonide, estrogen, sulfasalazine, and mesalamine); antineoplastic/antiproliferative/ anti-mitotic agents (such as paclitaxel, 5-fluorouracil, cisplatin, vinblastine, vincristine, epothilones, endostatin, angiostatin and thymidine kinase inhibitors); anesthetic agents (such as lidocaine, bupivacaine, and ropivacaine); anti-coagulants (such as D-Phe-Pro-Arg chloromethyl keton, an RGD peptide-containing compound, heparin, antithrombin compounds, platelet receptor antagonists, antithrombin antibodies, anti-platelet receptor antibodies, aspirin, prostaglandin inhibitors, platelet inhibitors, and tick antiplatelet peptides); vascular cell growth promoters (such as growth factor inhibitors, growth factor receptor antagonists, transcriptional activators, and translational promoters); vascular cell growth inhibitors (such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin); cholesterol-lowering agents; vasodilating agents; and agents which interfere with endogenous vasoactive mechanisms.

It should be understood that this disclosure is, in many respects, only illustrative. Changes may be made in details, particularly in matters of shape, size, and arrangement of steps without exceeding the scope of the invention. This may include, to the extent that it is appropriate, the use of any of the features of one example embodiment being used in other embodiments. The invention's scope is, of course, defined in the language in which the appended claims are expressed.

What is claimed is:

1. An endoprosthesis, comprising:
   an expandable framework configured to shift between a delivery configuration and a deployed configuration;
   wherein the expandable framework is continuous from a first end of the expandable framework to a second end of the expandable framework in the delivery and deployed configurations; and
   a covering comprising a plurality of polymeric cover segments disposed about at least a portion of the expandable framework;
   wherein a portion of each of the plurality of polymeric cover segments is fixedly attached to the expandable framework;
   wherein each of the plurality of polymeric cover segments is discontinuous from and longitudinally spaced apart from each other in the delivery configuration;
   wherein the plurality of polymeric cover segments longitudinally overlaps each other in the deployed configuration.

2. The endoprosthesis of claim 1, wherein each of the plurality of polymeric cover segments extends circumferentially about an entire circumference of the expandable framework.

3. The endoprosthesis of claim 1, wherein the covering extends between the first end of the expandable framework and the second end of the expandable framework.

4. The endoprosthesis of claim 1, wherein each of the plurality of polymeric cover segments includes an attachment band and a free end opposite the attachment band.

5. The endoprosthesis of claim 4, wherein the attachment band of each of the plurality of polymeric cover segments is oriented towards a first end of the expandable framework.

6. The endoprosthesis of claim 5, wherein the free end of each of the plurality of polymeric cover segments is oriented towards a second end of the expandable framework.

7. The endoprosthesis of claim 4, wherein the attachment band is discontinuously attached to the expandable framework.

8. An endoprosthesis, comprising:
   an expandable framework configured to shift between a delivery configuration and a deployed configuration;
   wherein the expandable framework is continuous from a first end of the expandable framework to a second end of the expandable framework in the delivery and deployed configurations; and
   a covering comprising a plurality of polymeric cover segments disposed about the expandable framework and extending longitudinally along the expandable framework;
   wherein the covering extends discontinuously with cover segments longitudinally spaced apart between a first end of the expandable framework and a second end of the expandable framework in the delivery configuration;
   wherein the covering extends continuously from the first end of the expandable framework to the second end of the expandable framework in the deployed configuration.

9. The endoprosthesis of claim 8, wherein the expandable framework includes a plurality of cells;
   wherein in the delivery configuration, at least some cells of the plurality of cells are completely uncovered by the covering; and
   wherein in the delivery configuration, the expandable framework is radially compressed and axially elongated.

10. The endoprosthesis of claim 9, wherein in the deployed configuration, all cells of the plurality of cells are completely covered by the covering.

11. The endoprosthesis of claim 8, wherein the expandable framework is self-expanding.

12. The endoprosthesis of claim 8, wherein each of the plurality of polymeric cover segments extends circumferentially about an entire circumference of the expandable framework.

13. The endoprosthesis of claim 8, wherein a free end of a first polymeric cover segment of an adjacent pair of polymeric cover segments is longitudinally spaced apart from of an attachment band of a second polymeric cover segment of the adjacent pair of polymeric cover segments in the delivery configuration.

14. The endoprosthesis of claim 13, wherein the free end of the first polymeric cover segment of the adjacent pair of polymeric cover segments is disposed radially outward of the attachment band of the second polymeric cover segment of the adjacent pair of polymeric cover segments in the deployed configuration.

15. An endoprosthesis, comprising:
   an expandable framework configured to shift between a delivery configuration and a deployed configuration, the expandable framework having a first end and a second end;
   wherein the expandable framework is continuous from a first end of the expandable framework to a second end of the expandable framework in the delivery and deployed configurations; and
   a covering comprising a plurality of polymeric cover segments disposed about at least a portion of the expandable framework;
   wherein a fixed end of each of the plurality of polymeric cover segments is fixedly attached to the expandable framework and a free end of each of the plurality of polymeric cover segments is free from attachment to the expandable framework;

wherein each of the plurality of polymeric cover segments is discontinuous from and longitudinally spaced apart from each other in the delivery configuration;

wherein the plurality of polymeric cover segments longitudinally overlaps each other in the deployed configuration such that the free end of one of the plurality of polymeric cover segments is positioned radially outward of the fixed end of an adjacent one of the plurality of polymeric cover segments.

16. The endoprosthesis of claim 15, wherein each of the plurality of polymeric cover segments extends circumferentially about an entire circumference of the expandable framework.

17. The endoprosthesis of claim 15, wherein each of the plurality of polymeric cover segments includes an attachment band at the fixed end thereof.

18. The endoprosthesis of claim 17, wherein the attachment band is discontinuously attached to the expandable framework.

19. The endoprosthesis of claim 15, wherein the expandable framework includes a plurality of cells;

wherein in the delivery configuration, at least some cells of the plurality of cells are completely uncovered by the covering.

20. The endoprosthesis of claim 19, wherein in the deployed configuration, all cells of the plurality of cells are completely covered by the covering.

* * * * *